United States Patent [19]

Russ et al.

[11] Patent Number: 5,030,446

[45] Date of Patent: Jul. 9, 1991

[54] OIL- AND TALC-FREE COSMETIC POWDER COMPOSITION

[75] Inventors: Julio G. Russ, Germantown, Tenn.; Salvatore J. Barone, Staten Island; Ralph A. Macchio, Monsey, both of N.Y.

[73] Assignee: Revlon, Inc., New York, N.Y.

[21] Appl. No.: 469,146

[22] Filed: Jan. 24, 1990

[51] Int. Cl.$^5$ .................. A61K 7/021; A61K 7/035
[52] U.S. Cl. ........................... 424/63; 424/64; 424/69; 424/78; 424/81
[58] Field of Search ............... 424/63, 64, 69, 78, 424/81; 514/844, 770, 769

[56] References Cited

U.S. PATENT DOCUMENTS

| | | | |
|---|---|---|---|
| 3,196,079 | 7/1965 | Blaustein | 424/63 |
| 4,246,257 | 1/1981 | Elliot et al. | 424/78 |
| 4,294,823 | 10/1981 | Elliott et al. | 424/78 |
| 4,435,220 | 3/1984 | Watanabe et al. | 106/415 |
| 4,648,908 | 3/1987 | Takasuka et al. | 106/417 |
| 4,659,562 | 4/1987 | Arraudeau et al. | 424/63 |
| 4,710,375 | 12/1987 | Takasuka et al. | 424/69 |
| 4,719,228 | 1/1988 | Rawlins | 514/456 |
| 4,772,331 | 9/1988 | Noguchi et al. | 106/417 |
| 4,783,333 | 11/1988 | Mercado et al. | 424/63 |
| 4,804,532 | 2/1989 | Busch et al. | 424/69 |
| 4,820,510 | 4/1989 | Arraudeau et al. | 424/63 |
| 4,837,011 | 6/1989 | Macchio et al. | 424/69 |
| 4,857,308 | 8/1989 | Fukasawa et al. | 424/63 |

FOREIGN PATENT DOCUMENTS 56-81512 7/1981 Japan .
61-257908 11/1986 Japan .

*Primary Examiner*—Thurman Page
*Assistant Examiner*—Susan S. Rucker
*Attorney, Agent, or Firm*—Julie Blackburn

[57] ABSTRACT

An oil-free and talc-free cosmetic powder composition which is useful as a foundation, blush, lipstick, eye shadow or mascara powder and which comprises a) about 0.00 to 90.00% of one or more coloring agents,
b) about 1.00 to 90.00% of silica,
c) about 1.00 to 90.00% of nylon,
d) about 1.00 to 90.00% of polymethylmethacrylate and
e) about 1.00 to 90.00 of mica, and wherein each of such a) to e) components is in the form of spherical beads having an average particle size in the range of about 1 to 20 microns.

9 Claims, No Drawings

OIL- AND TALC-FREE COSMETIC POWDER COMPOSITION

BACKGROUND OF THE INVENTION

1. Field of the Invention

The present invention relates to an oil- and talc-free cosmetic powder composition. This loose powder composition provides good adhesion to the skin without the use of oil or talc. The composition is useful as a foundation, blush, lipstick, eye shadow, mascara, or other cosmetic powder.

2. Prior Art

The prior art has disclosed various loose cosmetic powders employing microspheres of silica and/or polymeric materials to give a smooth, silky feel to the cosmetic powder. U.S. Pat. No. 4,837,011 shows spherical silica particles having a particle size of 6-20 microns. U.S. Pat. Nos. 4,246,257 and 4,294,823 show microspheres of polystyrene, polymethylmethacrylate or polyethylene having a particle size of 5-15 microns being used in a cosmetic for greasy or oily skin. However, these patents do not show a cosmetic product free of oil.

The prior art has also shown that these same microspheres of silica or polymeric material can be coated with a polymer (polyethylene), titanium dioxide, or other material. This is shown by published Japanese Patent Application 95395/1985 filed May 7, 1985. However, this published application does not show a cosmetic which is oil-free and talc-free. Another published Japanese Patent Application 81512/1981 discloses porous lipophilic silica having a particle size of 0.5-20 microns being used in a cosmetic powder. This published application also does not show an oil-free cosmetic powder.

It would be desirable if a combination of the spherical powders disclosed above could be used in oil-free and talc-free cosmetic powder. Talc is undesirable since it is drying to the skin. Oil is also undesirable since certain people are allergic to cosmetic oils and others have oily skin and thus would prefer an oil-free cosmetic which can still cling to the skin.

It is therefore an object of the present invention is to provide cosmetic powder compositions which are devoid of oils and talc.

A further object of the present invention is to provide a cosmetic powder composition which can be used for a wide variety of applications.

SUMMARY OF THE INVENTION

It has now been found that an oil-free and talc-free cosmetic powder can be prepared by combining small particles of cosmetic coloring agents, silica, nylon, polymethylmethacrylate and mica if at least the coloring agents are coated with a polyolefin resin, such as polyethylene, and the cosmetic powder has an average particle size of about 1 to 20 microns.

DETAILED DESCRIPTION OF THE INVENTION

The powdery cosmetic product which is free of oils and/or talc comprises, in weight %, a) about 0.01 to 90.00%, and preferably about 1 to 20%, of one or more treated cosmetic coloring agents, b) about 1.00 to 90.00%, and preferably about 10 to 30%, of silica, c) about 1.00 to 90.00%, and preferably about 10 to 30% of nylon, d) about 1.00 to 90.00%, and preferably about 5 to 15%, of polymethylmethacrylate (PMMA), and e) about 1.00 to 90.00%, and preferably about 10 to 30%, of mica.

Each of such a) to e) components is in the form of small particles, preferably of spherical shape, which have an average particle size of about 1 to 20 microns and preferably of about 1 to 15 microns and most preferably of about 2 to 5 microns.

At least the a) component is also treated with a thermoplastic polyolefin resin, such as polyethylene. Preferably, the c), d) and e) components are also treated with the resin coating. By being treated with the thermoplastic resin, it is meant that the particles of such a), c) and e) components of the composition of the present invention are coated with the polyethylene to the extent that the polyethylene comprises about 1 to 3 weight % of the thereby coated component, preferably 1 to 1.5 weight %.

The d) component, PMMA, may be titanated or treated with nylon. By being titanated, it is meant that the PMMA particles are coated with a titanating agent to the extent that the titanating agent comprises about 1 to 3 weight % of the coated component. The titanating agent is isopropyl triisostearoyl titantate. By being treated with nylon, it is meant that the PMMA particles are coated with a thermoplastic nylon polymer to the extent that the nylon comprises about 1 to 3 weight % of the coated component.

By being "oil-free", it is meant that the cosmetic powder has no mineral, vegetable, or animal-derived ingredients.

The combination of the a) to e) components of the present invention help the powdery product cling to the skin without the use of oils while providing a smooth feel when on the skin.

The compositions of the present invention may also contain, in weight percent, about 0.1 to 2%, and preferably about 0.2 to 1.5%, of one or more preservatives such as methyl paraben, butyl paraben, propyl paraben, phenoxyethanol, benzoic acid, imidazolidinyl urea, and other conventional preservatives, and preferably about 0.05 to 0.1%, of one or more antioxidants such as BHA, about 0.01 to 10% of other optional filler components, such as polyethylene, magnesium carbonate, and methylcellulose.

The total weight percent of the compositions of the present invention is 100%.

The components of the compositions of the present invention are dry blended together using conventional cosmetic powder blending apparatus and procedures.

The following examples are merely illustrative of the scope of the present invention and are not intended as a limitation thereon.

EXAMPLES

The following formulations were used to prepare two of the cosmetic powder compositions of the present invention which adhered well to the skin and provided a smooth feel.

| Component | Weight % Of Component In Composition | |
|---|---|---|
| | I | II |
| PE treated TiO₂ | 13.7 | 14.0 |
| PE treated mica | 29.2 | 30.0 |
| Titanated PMMA¹ | 11.4 | 11.4 |
| silica | 11.4 | 11.4 |
| PE treated nylon | 27.5 | 27.4 |
| PE treated Red I/O | 1.2 | 1.2 |
| PE treated yellow I/O | 2.6 | 2.6 |
| PE treated blue I/O | 0.2 | 0.2 |
| methyl paraben | 0.3 | 0.3 |
| propyl paraben | 0.1 | 0.1 |
| butyl paraben | 0.1 | 0.1 |
| BHA | 0.1 | 0.1 |
| phenoxyethanol | 1.0 | 1.0 |
| benzoic acid | 0.2 | 0.2 |
| methyl cellulose | 1.0 | — |
| | 100.0 | 100.0 |

¹titanated with isopropyl triisostearoyl titantate

The compositions of the present invention may be used in the form of loose powders or in the form of pressed articles such as compacts, tablets, sticks, and pellets.

Furthermore, the compositions may be used as matte or frosted products.

What is claimed is:

1. An oil-free and talc-free cosmetic powder composition comprising, in weight %,
   a) about 0.01 to 90.00% of one or more treated coloring agents,
   b) about 1.00 to 90.00% of silica
   c) about 1.00 to 90.00% of nylon
   d) about 1.00 to 90.00% of polymethylmethacrylate and
   e) about 1.00 to 90.00% of mica, each of said a) to e) components being in the form of small particles having an average particle size in the range of about 1 to 20 microns, and
   at least said a) component being treated with polyethylene.

2. A composition as in claim 1 in which the one or more of said c), d) and e) components are treated with polyethylene.

3. A composition as in claim 1 in which said d) component is titanated with isopropyl triisostearoyl titanate.

4. A composition as in claim 1 which further comprises, in weight %,
   f) about 0.1 to 2% of one or more preservatives
   g) about 0.01 to 0.2% of one or more antioxidants
   h) about 0.1 to 10% of one or more fillers other than said b) to d) components.

5. A composition as in claim 1 comprising
   a) about 1 to 20% of one or more coloring agents, with one or more of said coloring agents being treated with polyethylene,
   b) about 10 to 30% of silica,
   c) about 10 to 30% of polyethylene treated nylon
   d) about 5 to 15% of titanated polymethylmethacrylate and
   e) about 10 to 30% of polyethylene treated mica.

6. A composition as in claim 5 in which each of said a) to e) components has an average particle size of 1 to 15 microns.

7. A composition as in claim 5 in which each of said a) to e) components has an average particle size of 2 to 5 microns.

8. A composition as in claim 6 which is a foundation, blush, lipstick, eye shadow or mascara powder.

9. A composition as in claim 7 which is a foundation, blush, lipstick, eye shadow or mascara powder.

* * * * *